(12) United States Patent
Hennig (10) Patent No.: US 8,423,149 B2
(45) Date of Patent: Apr. 16, 2013

(54) SYSTEM AND METHOD FOR THE REMOTE PROGRAMMING OF A PROGRAMMABLE PERSONAL MEDICAL DEVICE

(75) Inventor: Carsten Hennig, Berlin (DE)

(73) Assignee: BIOTRONIK CRM Patent AG (CH)

( * ) Notice: Subject to any disclaimer, the term of this patent is extended or adjusted under 35 U.S.C. 154(b) by 1158 days.

(21) Appl. No.: 12/165,733

(22) Filed: Jul. 1, 2008

(65) Prior Publication Data

US 2009/0024178 A1 Jan. 22, 2009

(30) Foreign Application Priority Data

Jul. 19, 2007 (DE) .......................... 10 2007 033 993

(51) Int. Cl.
*A61N 1/08* (2006.01)
(52) U.S. Cl.
USPC .................................. 607/60; 607/30; 607/31
(58) Field of Classification Search .................... 607/30, 607/31, 60
See application file for complete search history.

(56) References Cited

U.S. PATENT DOCUMENTS

| | | | |
|---|---|---|---|
| 7,043,305 B2 * | 5/2006 | KenKnight et al. ............ | 607/60 |
| 2002/0040234 A1 * | 4/2002 | Linberg ........................ | 607/32 |
| 2003/0088290 A1 | 5/2003 | Spinelli | |
| 2003/0088295 A1 * | 5/2003 | Cox ............................... | 607/60 |
| 2004/0122488 A1 | 6/2004 | Mazar et al. | |
| 2004/0199217 A1 | 10/2004 | Lee | |
| 2005/0032511 A1 | 2/2005 | Malone et al. | |
| 2005/0245992 A1 | 11/2005 | Persen et al. | |
| 2005/0251227 A1 | 11/2005 | Khoo et al. | |
| 2006/0122863 A1 | 6/2006 | Gottesman | |
| 2006/0212092 A1 | 9/2006 | Pless et al. | |

FOREIGN PATENT DOCUMENTS

| WO | WO 2006/130060 A1 | 12/2006 |
|---|---|---|
| WO | WO 2007/081829 A | 7/2007 |

* cited by examiner

*Primary Examiner* — Tammie K Heller
(74) *Attorney, Agent, or Firm* — Craig A. Fieschko, Esq.; DeWitt Ross & Stevens S.C.

(57) ABSTRACT

The invention relates to a system and a method for the remote programming of a programmable personal medical device (10, 10'), in particular an implantable medical device such as a cardiac pacemaker, defibrillator, or the like, selecting (61) of a personal medical device, compiling (63) of a programming instruction (50) by accepting inputs of a user, and checking (63) the inputs for plausibility and compatibility with the personal medical device in a programming device (20), transmitting (65) the programming instruction to a patient intermediary device (30) tuned to the personal medical device via at least one indirect connection, receiving (67) of the programming instruction by the patient intermediary device, and transmitting of the programming instruction to the personal medical device, and accepting (69) of the programming instruction by a programmable controller of the personal medical device being provided.

21 Claims, 6 Drawing Sheets

SYSTEM AND METHOD FOR THE REMOTE PROGRAMMING OF A PROGRAMMABLE PERSONAL MEDICAL DEVICE

FIELD OF THE INVENTION

The invention relates to a system for the remote programming of a programmable personal medical device, in particular an implantable medical device such as a cardiac pacemaker, defibrillator, or the like.

BACKGROUND OF THE INVENTION

To ensure the most optimum possible care of the patient and optimum operation of a cardiac pacemaker or similar device, it is often necessary in practice to adapt the programming of the device on the basis of the course of the aftercare and the current constitution of the patient.

In some cases, a programming device is used for reprogramming the implant, which transmits an altered program for the implant directly into the implant via a typically wireless data communication. For this purpose, programming device and implant must be in a close spatial proximity to one another. This makes it necessary for the patient to visit his physician, a hospital, or another aftercare ward, i.e., a location at which the programming device is kept. The physician and patient must then necessarily be located at the same place at the same time. This necessity is often perceived as burdensome, and in particular it restricts the mobility of the patient.

The present invention may provide a system for the remote programming of a programmable personal medical device, in which a program transmission into the programmable personal medical device is possible without physician and patient having to meet. Additionally, the physician may retain the capability of using his familiar programming device.

The invention is based on the insight that a patient intermediary device, as is typically already used for transmitting telemetry data of a device such as a cardiac pacemaker to a service center, may be equipped with a further functionality of a relay station, to transmit a programming instruction prepared in a programming device into the personal medical device, without it being necessary for the wearer of the personal medical device to seek out the programming device. The patient intermediary device is located at a distance from the programming device in an area which is at least regularly sought out by the wearer of the personal medical device, so that the patient intermediary device may be used effectively as an intermediate station for the remote programming of the personal medical device.

Further advantageous designs of the invention are set forth in the claims and in the following description of the preferred exemplary embodiments.

BRIEF DESCRIPTION OF THE DRAWINGS

The invention is explained in greater detail hereafter on the basis of preferred exemplary embodiments with reference to the appended figures. In the figures.

DETAILED DESCRIPTION OF PREFERRED VERSIONS OF THE INVENTION

Figure 1:
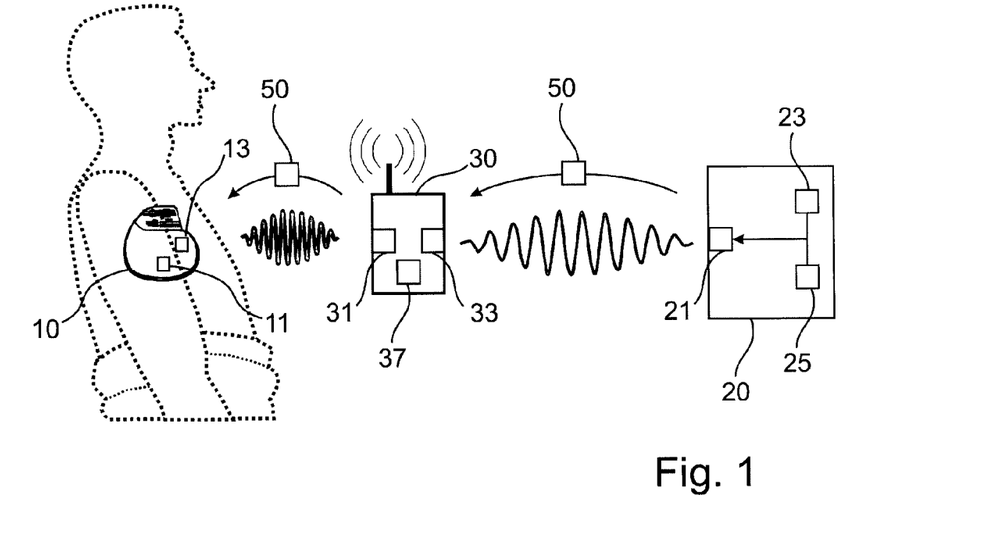
FIG. 1 shows a first system according to the invention for the remote programming of an implant.

FIG. 1 schematically shows a patient having an implant 10. A patient intermediary device 30 is positioned in proximity to the patient and thus in proximity to the implant 10. The programming device 20 is located at a distance from the patient and from the patient intermediary device 30. Programming device 20 and patient intermediary device 30 are tuned to the particular implant 10 at least for the duration of the remote programming.

The implant 10 has a first interface 11 and a programmable controller 13. The implant 10 preferably additionally has an authentication unit.

The patient intermediary device 30 is equipped with a first interface 31 and a second interface 33. The patient intermediary device 30 preferably additionally has an authentication unit 37.

The programming device 20 has a first interface 21, a programming unit 23, and an input unit 25.

The input unit 25 is designed for the purpose of accepting inputs of a user, the input unit 25 being coupled to the programming unit 23 to prepare a programming instruction together with the programming unit 23. The programming unit 23 is implemented to generate a new or a revised program having a suitable set of control parameters for the personal medical device 10 on the basis of the inputs and to check this program for plausibility and compatibility with the personal medical device 10. Only a program which meets the particular desired requirements for plausibility and compatibility is permitted for a programming instruction.

The first interface 21 of the programming device 20 and the second interface 33 of the patient intermediary device 30 are designed in the present case for a transmission of a data set 50 from the programming device 20 to the patient intermediary device 30. According to FIG. 1, the interfaces 21, 33 are designed for a connection according to a GSM specification, i.e., a wireless radio transmission. Alternatively thereto, a connection via a land-based telephone line or another suitable type of communication may also be used. Combinations of different protocols and/or specifications are also possible. For example, the communication may also occur via a WLAN network to which the programming device is connected, a land-based data line, and a Bluetooth connection between the land-based data line and the patient intermediary device 30, unidirectional or bidirectional connections being possible.

The patient intermediary device 30 receives the data set 50, the authentication unit 37 checking the data set 50 for the presence of a valid authentication. The data set 50 having the programming instruction (see FIG. 4) is only transmitted via the first interface 31 of the patient intermediary device 30 and the first interface 11 of the implant 10 to the implant 10 when the presence of a valid authentication in the data set 50 is confirmed by the authentication unit 37. In this case, it may be provided that only the part of the data set 50 which corresponds to the programming instruction is transmitted, i.e., the authentication element of the data set 50, is not also transmitted. The programming instruction is received by the programmable controller 13 of the implant 10 and processed in a suitable and known way.

Figure 2:
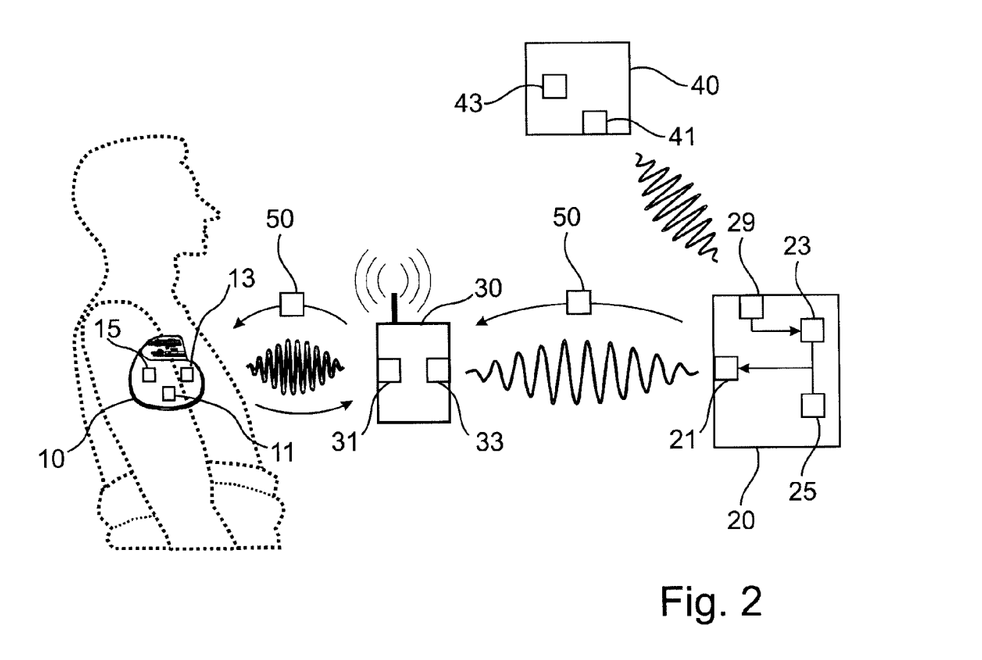
FIG. 2 shows a second embodiment of a system according to the invention for the remote programming of an implant.

FIG. 2 shows a further exemplary embodiment of a system for remote programming according to the invention. The system shown in FIG. 2 partially corresponds to the system shown in FIG. 1, with similar elements using the same reference numerals. The embodiment shown in FIG. 2 differs from the system from FIG. 1 in that the system of FIG. 2 has a service center 40 having a first interface 41 and a data memory 43. The interface 41 is used for connecting the service center 40 to the programming device 20. The data memory 43 contains data which relates to the implant 10.

The programming device 20 has a second interface 29 which is provided for producing a connection to the service center 40.

In the preparation and checking of a programming instruction, a query is directed to the service center via the interfaces 29 and 41, to transmit data stored in the data memory 43 in regard to the implant 10 to the programming device 20.

The programming instruction is prepared in a known manner using the data transmitted from the data memory 43.

The programming instruction which is embedded in the data set 50 is transmitted in accordance with the transmission as was described with reference to FIG. 1.

In the present embodiment here, the implant 10 has a comparison unit 15. In the preparation of the programming instruction and the provision of the data from the data memory 43, an identification of a prior program of the implant 10 is generated, which is appended to the programming instruction in the data set 50. The comparison unit 15 is implemented to compare the identification appended to this programming instruction with the current program of the controller. If this comparison has the result that the programming instruction was not prepared on the basis of the current program active in the implant, the programming instruction is rejected. On the other hand, if the comparison shows that the current program, or a prior program corresponding to the current program, was the foundation of the programming instruction, the programming instruction is accepted and processed by the controller 13. Information on the comparison result for the acceptance or rejection of the programming instruction, respectively, is transmitted via the interfaces 11 and 31 to the patient intermediary device 30. This information may be stored here for a later query or transmitted directly to a suitable location for checking, for example.

Figure 3:
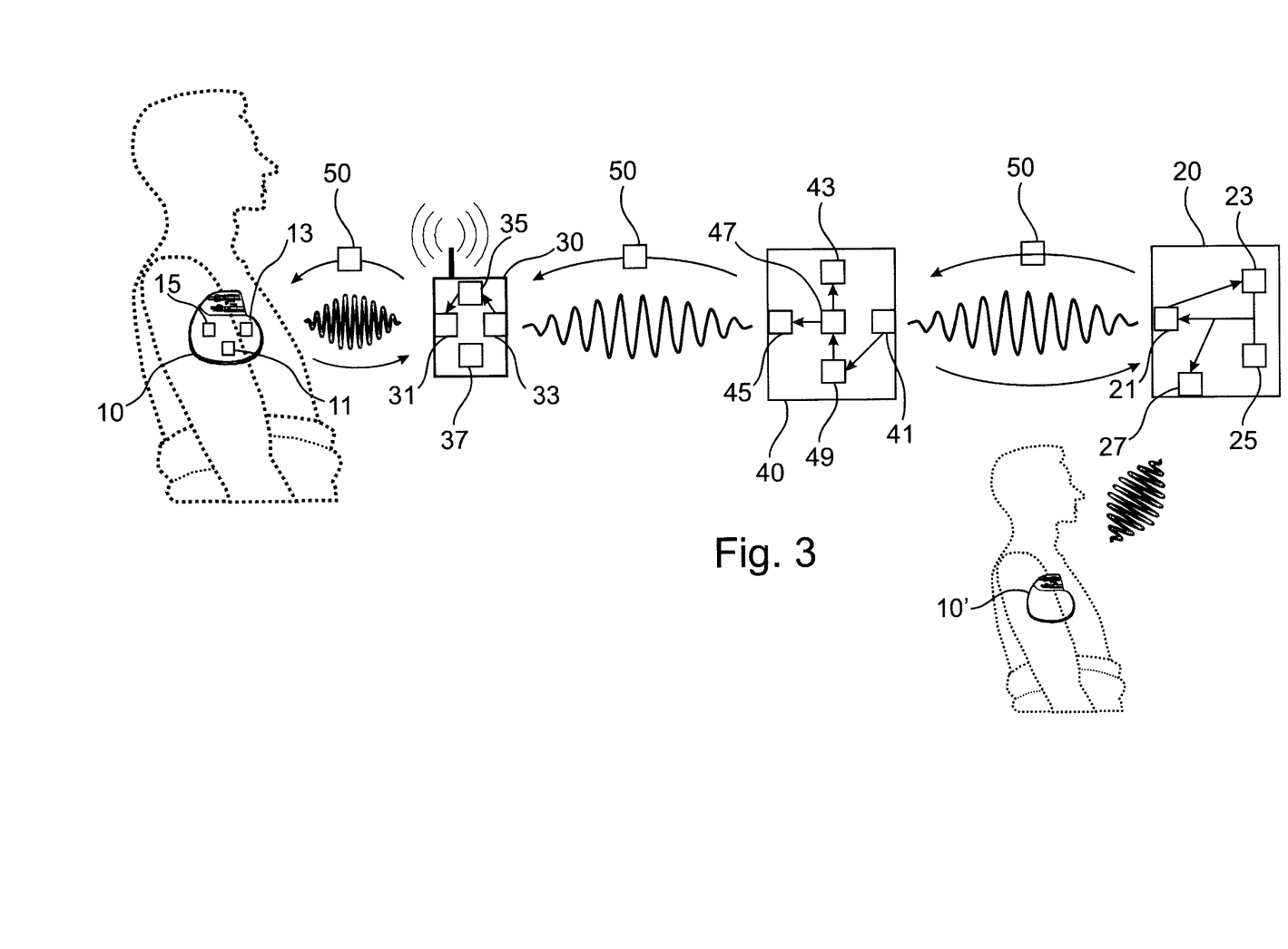
FIG. 3 shows a third embodiment of a system according to the invention for the remote programming of an implant.

FIG. 3 shows a further embodiment of the present invention.

The patient is equipped with an implant 10, which has a first interface 11, a controller 13, and a matching unit 15. The implant 10 corresponds to the implant shown in FIG. 2.

The patient intermediary device 30 has a first interface 31, a second interface 33, a program memory 35, and an authentication unit 37. First and second interfaces 31, 33 and authentication unit 37 correspond to the units described above. The programming memory 35 is connected to the interface 33 and is used for the purpose of at least temporarily buffering a received data set and/or a received programming instruction. The buffered programming instruction and/or the buffered data set is relayed to the implant 10 at a suitable time via the interface 31. In this manner, it is possible for the patient intermediary device to receive a programming instruction and retain it until the patient having the implant 10 comes back into the communication range of the interface 31, so that even during an absence of the patient, the programming instruction may reach the patient intermediary device and be transmitted to the implant upon return of the patient and/or the implant to the patient intermediary device.

According to the embodiment shown in FIG. 3, the service center 40 is provided as a further intermediate station between the programming device 20 and the patient intermediary device 30. The service center 40 has a first interface 41, second interface 45, a data memory 43, a data unit 47, and a verification unit 49. The interface 41 is used for communication with the programming device 20. A connection may be established between the service center 40 and the patient intermediary device 30 via the interface 45 in combination with the second interface of the patient intermediary device 33 to be able to transmit a data set 50 from the service center 40 to the patient intermediary device 30.

The service center 40 receives a programming instruction which is embedded in a data set 50 via the interface 41. The received data set and/or the received programming instruction is analyzed by the data unit 47, predetermined data being added on the basis of the programming instruction to the data stored in the data memory 43, which may also be associated with the personal medical device. In this manner, for example, documentation of the programming instructions sent to the implant 10 may be retained in the data memory 43. The verification unit 49 is connected upstream from the data unit in the embodiment shown in FIG. 3 and is implemented for the purpose of performing a verification of the programming device before the data of the programming instruction is processed further. This increases the general security, so that intentional or unintentional maloperations may be avoided. The data set and/or programming instruction processed and/or checked by verification unit 49 and/or data unit 47 is provided for the purpose of being transmitted via the second interface 45 of the service center 40 to the patient intermediary device 30.

The programming device 20 has a first interface 21, a third interface 27, a programming unit 23, and an input unit 25. Programming unit 23 and input unit 25 are implemented for the purpose, similarly to the embodiment described in FIG. 2, of requesting and receiving data with reference to the implant 10 from the service center 40. For this purpose, a verification of the data request and/or the authorization of the programming device to receive the desired data is performed using the verification unit 49. If the verification unit 49 permits the transmission of the data, the data output from the data memory 43 is transmitted via the connection established using the interfaces 41 and 21 between the service center 40 and the programming device 20 to the programming device 20. The data is used by the programming device 20, more precisely by the programming unit 23 and the input unit 25, to prepare a programming instruction, similarly to the embodiment from FIG. 2.

The third interface 27 of the programming device 20 is designed to establish a connection to an implant 10' located in close proximity and is used for transmitting a programming instruction prepared by the programming device 20 for the implant 10' to the implant 10'. A data query may also be provided in the data memory 43 of the service center 40 in the way described above for the preparation of the programming instruction for the implant 10'. The programming device as shown in FIG. 3 has a double functionality. On one hand, it may be used for remote programming via the service center 40 and the patient intermediary device 30 of the implant 10. On the other hand, an implant 10' may be programmed directly by the programming device 20.

Various embodiments of a system for the remote programming of an implant, for example, such as the embodiments shown in FIGS. 1 through 3, may be combined in a joint system for remote programming as alternative embodiments. In this combined system, different communication pathways, which supplement one another, are available for the transmission and/or transfer of the programming instruction from the programming device to the implant. In addition, multiple implants and multiple patient intermediary devices may also be provided in a system according to the invention, different communication pathways and/or embodiments of the system being able to be used depending on the implant and/or the patient intermediary device. Multiple service centers may also be provided in parallel to one another, which optionally communicate with one another and may thus form a modularly constructed service center.

The system according to the invention may also provide multiple programming devices, which are used in parallel or alternatively to one another.

Figure 4:
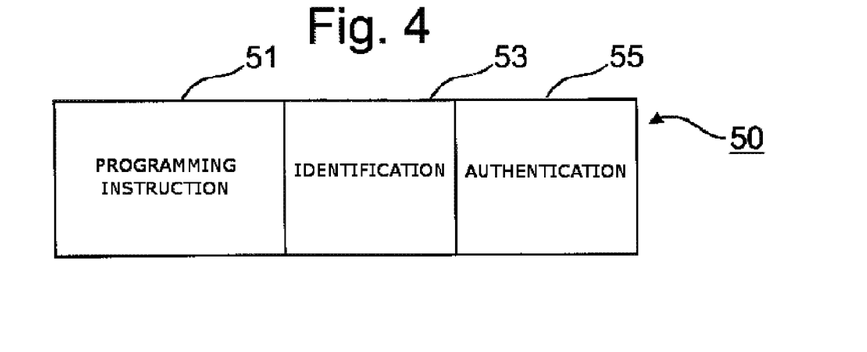
FIG. 4 shows a data set used in the system shown in FIG. 3.

FIG. 4 schematically shows a data set 50, which may be used in the form shown in a system as shown in FIG. 3, for example. The data set 50 comprises a programming instruction 51, an identification 53, and an authentication 55. The patient intermediary device 30 and/or the personal medical device 10, 10' is equipped with an authentication unit 37 for authentication. The identification 53 may be a unique program number, which refers to a prior program, for example. The authentication may comprise the specification of a password or the combination of a user identification and a password. Other identifications or authentications known to those skilled in the art are also possible.

Figure 5:
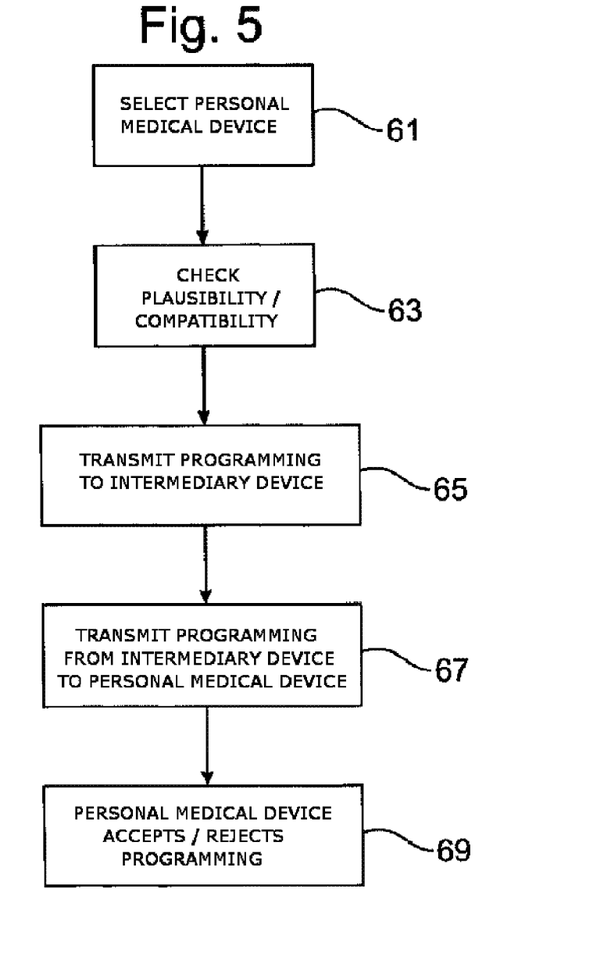
FIG. 5 shows a schematic sequence of a method according to the invention for the remote programming of a programmable personal medical device.

FIG. 5 schematically shows a method sequence according to the invention of a method for the remote programming of a programmable personal medical device. After selecting a personal medical device (step 61), a programming instruction is prepared, in which user inputs are compiled. The programming instruction is additionally checked for plausibility and compatibility with the selected personal medical device, so that only a plausible and compatible programming instruction is processed further (step 63). The prepared programming instruction is transmitted to a patient intermediary device tuned to the personal medical device, depending on the application, an indirect connection being used, i.e., intermediate stations being provided, or a direct connection being produced between the patient intermediary device and the programming device (step 65). The programming instruction is received by the patient intermediary device and transmitted to the personal medical device (step 67). Finally, the programmable controller of the personal medical device accepts the programming instruction, which includes processing or rejection of the programming instruction (step 69).

In a further exemplary embodiment of the present invention, the programming device is linked to a hospital network via WLAN or wired LAN and has a connection to a home monitoring service center server (HMSC server) via the hospital network. The physician inputs his HMSC access data at the programming device, upon which the programming device presents the physician with a list of the patients who are assigned to the physician in the HMSC and are enabled for remote programming. After the selection of the appropriate patient and/or the appropriate implant, the last known program of the implant is displayed in the user interface familiar to the physician, the programming device being able to receive the last program from the HMSC or have it stored itself. After the revision and/or adaptation of the program, it is transmitted from the programming device to the HMSC and transmitted from there to the patient intermediary device of the appropriate patient. A unique program number of the old, i.e., still current programming is also sent. The new program on the basis of the transmitted programming instruction is only accepted in the implant when the program number stored and/or determined in the implant itself corresponds to the program number also transmitted.

According to a further alternative or supplementary aspect, the programming device is connected via a mobile wireless network, for example, by GSM, directly to the server of the HMSC, the sequence of the remote programming occurring as described above. As a further alternative and/or supplement, the programming device may be connected via a mobile wireless connection or the Internet directly to the patient intermediary device. In this case the detour via the server of the HMSC is dispensed with, the HMSC initially being dispensed with as the element of access control and documentation of the reprogramming. The HMSC may thus initially not provide any information about the current programming. However, it is possible that a further connection to the HMSC is established in parallel to the connection with the patient intermediary device, which may then be used, for example, for documentation of the reprogramming or a supplementary access check. In order that the programming device may connect directly to the patient intermediary device, the programming device requires an identification number, such as a telephone number of the patient intermediary device. The desired implant was preferably already programmed directly once previously using a programming device and set up for the remote programming together with the patient intermediary device, a password protection or another access control being able to be set up, for example.

Figure 6:
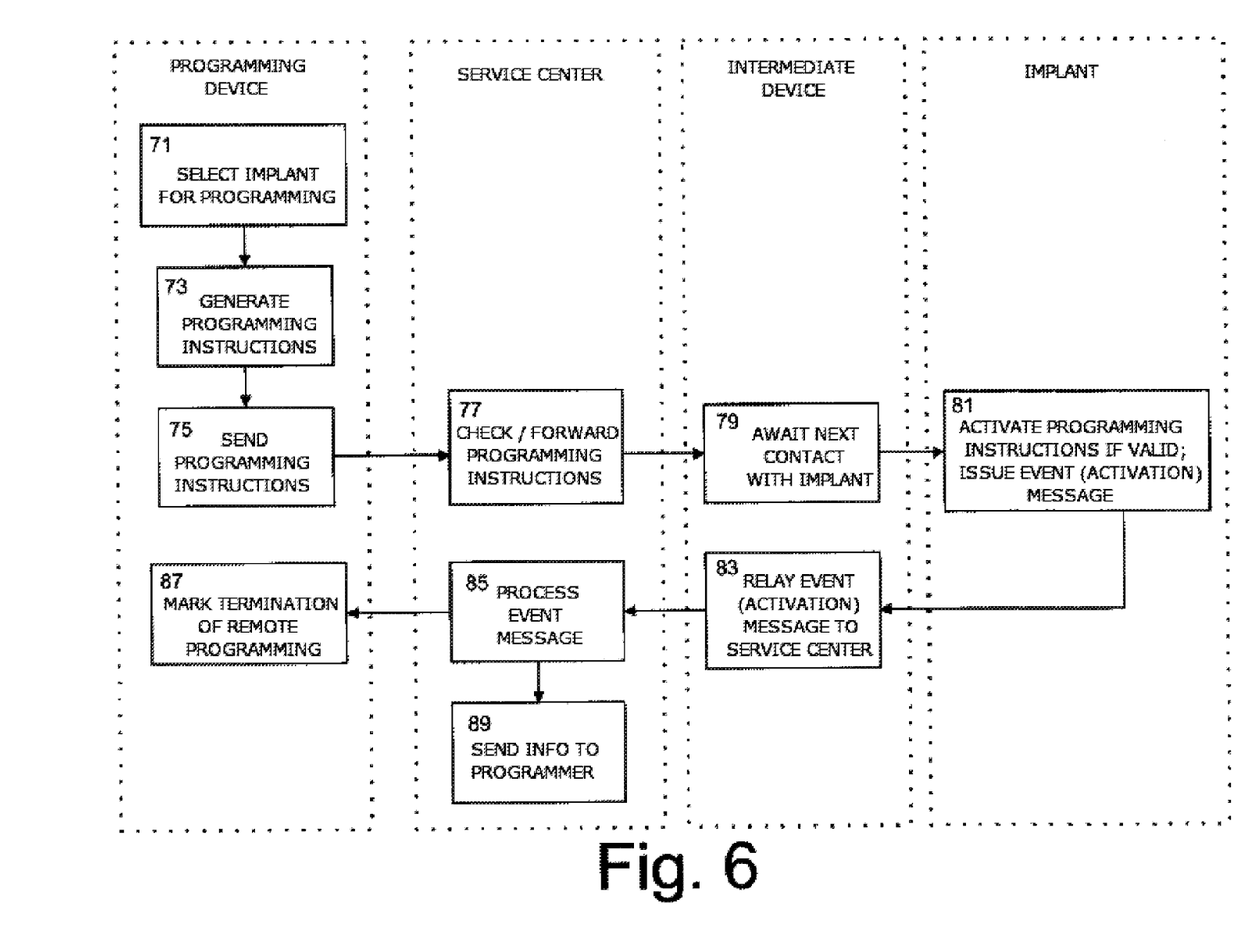
FIG. 6 shows a schematic sequence of remote programming according to the invention.

FIG. 6 schematically shows a method sequence during asynchronous remote programming by the programming device via a service center. In step 71, a physician selects a previously queried implant for remote programming. In step 73, parameter changes including a plausibility check, for example, for parameter conflicts, as well as a compatibility check are performed. A suitable programming instruction thus results. In step 75, the physician inputs his access data for the service center, such as an HMSC, and sends off the new parameter set, i.e., the programming instruction. A transmission to the service center may be performed, for example, by LAN, WLAN, GSM, or similar communication pathways. In the service center in step 77, the authorization is checked and the programming instruction is processed for relay and documented in the HMSC databank. The required data is relayed to the patient intermediary device by mobile wireless or by fixed network telephone line, for example, by GSM or landline. In step 79, the patient intermediary device accepts the program and waits for the next contact to the target implant. The programming instruction is preferably transmitted by MICS (medical impact communication service) to the implant with the next contact to the target implant. In step 81, the validity of the program is checked in the implant and the program is activated if needed. The program may also provide only temporary activation. In accordance with the output of the validity check and the activation, an event message is transmitted via the successful or rejected remote programming to the patient intermediary device. The patient intermediary device relays the event message to the service center in step 83. The event message about the remote programming is processed in step 85. Information in regard to the event message goes to the programming device, which marks the remote programming as terminated in step 87. The relay of the information about the event message for step 87 is performed, for example, at the next possible opportunity and may be performed by LAN, WLAN, or GSM. Further information is activated in the service center itself, which sends information in step 89 to the physician via the HMSC.

Figure 7:
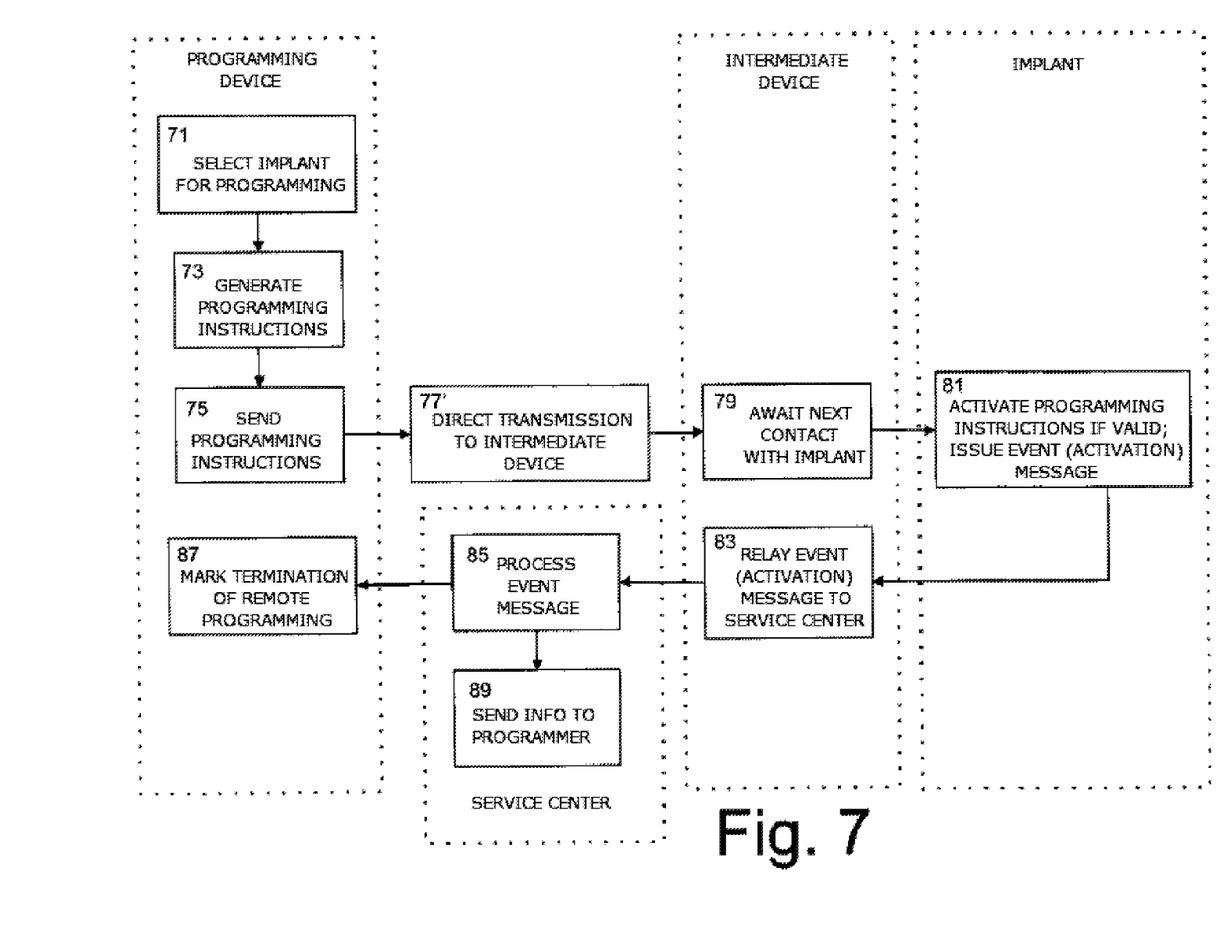
FIG. 7 shows a further sequence of remote programming according to the invention.

An alternative sequence for asynchronous remote programming is schematically shown in FIG. 7. In this case, the remote programming is performed without primary engagement of a service center during the transmission of the programming instruction to the patient intermediary device. The sequence shown in FIG. 7 largely corresponds to the sequence shown in FIG. 6. Instead of the transmission to the service center, according to FIG. 7, a transmission is performed by mobile wireless via a corresponding telephone company in step 77' to the patient intermediary device, the final connection to the patient intermediary device also being able to be produced via a land-based telephone line. The remaining sequence of the programming procedure corresponds to that described on the basis of FIG. 6.

Figure 8:
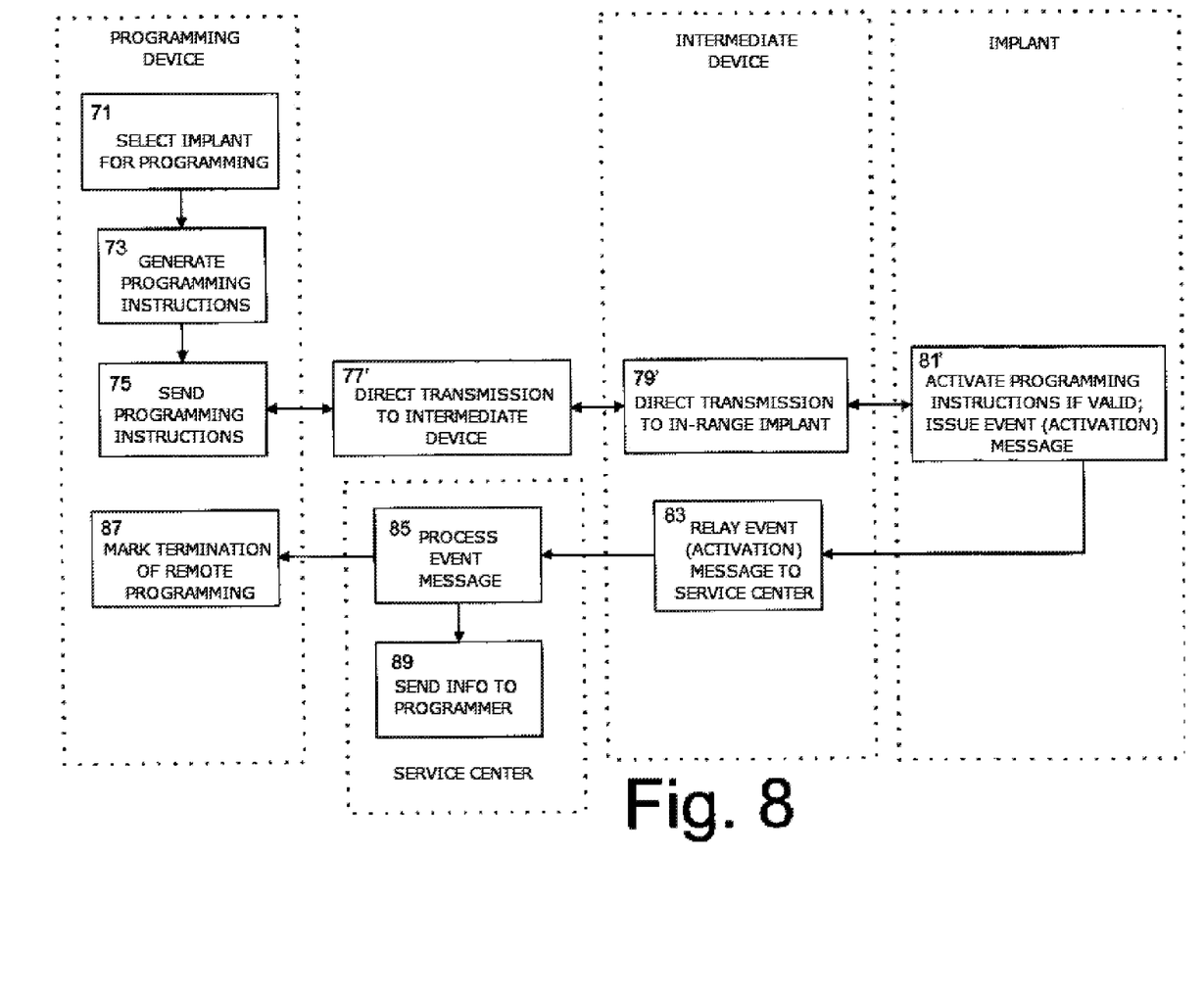
FIG. 8 shows a third sequence of remote programming according to the invention.

FIG. 8 schematically shows a sequence of synchronous remote programming using a coupling between programming device and patient intermediary device without engaging a service center for transmitting data to the patient intermediary device. The sequence shown in FIG. 8 again fundamentally corresponds to the asynchronous sequence as shown in FIG. 7. A telephone company or a similar provider for transmitting data again relays the programming instruction from the programming device to the patient intermediary device in step 77'. However, in step 79', after the program is accepted, the program is relayed directly to the implant, which requires that the implant is within the range of the patient intermediary device. A confirmation about the relay to the implant is transmitted directly, on the same pathway on which the programming instruction also reached the patient intermediary device, back to the programming device. Correspondingly, a confirmation may also be sent, on the corresponding pathway to the programming device, that the programming instruction has been found valid and the program was activated or that the program activation was denied (step 81'). As in the sequences described above, an event message is sent about successful remote programming or also about denied remote programming to the patient intermediary device and a service center, by which information is sent to the physician (steps 83, 85, 89). Because the physician himself receives information about whether the programming was successfully terminated as a result of the synchronicity of the remote programming on the programming device, the physician may also terminate the remote programming himself in step 87.

The preparation of the new program including the checking of all possible conflicts is performed in a way typical for a physician on the programming device as previously. Restrictions in the setting of the parameters (e.g., limiting of the setting range), which result from possible safety considerations in regard to the tele-transmission, are checked in the programming device. A valid parameter set for the tele-programming may, as an alternative to the transmission by close range telemetry, be transferred to a relay station for further distribution to the target implant. The programming device then transmits the program, for example, either directly to the patient intermediary device or via a web platform, for which it is equipped with a suitable network interface (e.g., WLAN, LAN, GSM, UMTS, Bluetooth). The transmission of the program may be performed asynchronously or synchronously. In synchronous transmission, a connection exists between the patient and his patient intermediary device during the program transmission from physician/programming device. The program transmission and possibly an acknowledgment occur immediately. In asynchronous transmission, the revised program is initially stored in the patient intermediary device and first transferred into the implant the next time the implant is in the communication range of the patient intermediary device. No chronological timing between physician and patient is necessary, however, it is initially not predetermined when the program will be active in the implant.

The remote programming preferably requires that the current program of the implant is known, i.e., the programming device may display the last known program to the physician, so that he may make his therapy decision on this basis and correctly. The remote transmission of the program additionally contains a method by which it is ensured that the new program is only accepted in the implant if the current implant program responds to the program expected by the programming device.

What is claimed is:

1. A system for the remote programming of a programmable personal medical device, in particular an implantable medical device such as a cardiac pacemaker, defibrillator, or the like, including:
   i. a programming device (20),
   ii. a patient intermediary device (30),
   iii. a programmable personal medical device (10, 10'), the programming device (20), patient intermediary device (30), and programmable personal medical device (10, 10') being spaced from each other, wherein:
   a. the programming device (20) includes:
      (1) a programming unit (23) accepting input of programming instructions for the programmable personal medical device (10, 10');
      (2) a programming device first interface (21) in communication with the patient intermediary device (30) and transmitting the programming instructions thereto;
   b. the patient intermediary device (30) includes:
      (1) an intermediary device second interface (33) receiving the programming instructions from the programming device (20),
      (2) an intermediary device first interface (31) transmitting the programming instructions to the personal medical device (10, 10'),
   c. the personal medical device (10, 10') includes:
      (1) a personal device first interface (11) receiving the programming instructions from the intermediary device first interface (31),
      (2) a programmable controller (13) controlling functions of the personal medical device (10, 10') in accordance with the programming instructions received by the personal device first interface (11),
   and wherein:
   I. the programming device (20) is configured to append an identification (53) of a prior program to the programming instructions,
   II. the personal medical device (10, 10') includes a comparison unit (15) configured to compare the identification appended to the programming instructions to the current program of the programmable controller (13), and
   III. the programmable controller (13) is configured to reject the programming instructions if comparison results are negative.

2. The system of claim 1 wherein the programming device first interface (21) transmits the programming instructions to the patient intermediary device (30) via a service center (40), the service center (40) including:
   a. a service center first interface (41) receiving the programming instructions from the programming device first interface (21), and
   b. a service center second interface (45) transmitting the programming instructions to the intermediary device second interface (33).

3. The system of claim 1:
 a. further including a service center (40) having:
  (1) a service center first interface (41) configured to connect the service center (40) in communication with the programming device (20), and
  (2) a data memory (43) configured to store data associated with at least one personal medical device,
 b. wherein:
  (1) the programming device first interface (21) is configured to provide communication between the programming device (20) and the intermediary device second interface (33),
  (2) the programming device (20) further includes a programming device second interface (29) allowing communication between the programming device (20) and the service center (40),
  (3) the programming unit (23) and the input unit (25) cooperate to request data associated with the personal medical device (10, 10') from the service center (40).

4. The system of claim 3 wherein:
 a. the service center (40) has a service center second interface (45) configured to provide communications between the service center (40) and the patient intermediary device (30),
 b. the programming device (20) is configured to transmit the programming instructions to the service center (40), and
 c. the service center (40) is configured to transmit the received programming instructions to the patient intermediary device (30).

5. The system of claim 1 wherein the programming device first interface (21) is configured to transmit the programming instructions to the patient intermediary device (30) via a service center (40), the service center (40) including:
 a. a service center first interface (41) configured to receive the programming instructions from the programming device first interface (21), and
 b. a service center second interface (45) configured to transmit the programming instructions to the intermediary device second interface (33).

6. The system of claim 1 wherein the patient intermediary device first interface (31) and the personal device first interface (11) are configured to wirelessly communicate at a range of up to approximately 5 meters.

7. A system for the remote programming of a programmable personal medical device, in particular an implantable medical device such as a cardiac pacemaker, defibrillator, or the like, including:
 i. a programming device (20),
 ii. a service center (40)
 iii. a patient intermediary device (30),
 iv. a programmable personal medical device (10, 10'),
 wherein:
 a. the programming device (20) accepts input of programming instructions for the programmable personal medical device (10, 10'), and thereafter transmits the programming instructions;
 b. the service center (40) receives the programming instructions from the programming device (20), and thereafter transmits the programming instructions;
 c. the patient intermediary device (30) receives the programming instructions from at least one of:
  (1) the service center (40), and
  (2) the programming device (20),
  and thereafter transmits the programming instructions to the personal medical device (10, 10'),
 d. the personal medical device (10, 10') includes a programmable controller (13) for controlling functions of the personal medical device (10, 10') in accordance with the programming instructions received from the patient intermediary device (30),
 wherein:
 I. the programming device (20) is configured to append an identification (53) of a prior program to the programming instructions,
 II. the personal medical device (10, 10') includes a comparison unit (15) configured to compare the identification appended to the programming instructions to the current program of the programmable controller (13), and
 III. the programmable controller (13) is configured to reject the programming instructions if comparison results are negative.

8. The system of claim 7, wherein:
 a. the service center (40) has:
  (1) a service center first interface (41) configured to connect the service center (40) in communication with the programming device (20), and
  (2) a data memory (43) configured to store data associated with at least one personal medical device, and
 b. wherein:
  (1) the programming device (20) is configured to communicate with the service center (40),
  (2) the programming device (20) is configured to request data associated with the personal medical device (10, 10') from the service center (40).

9. The system of claim 8 wherein:
 a. the service center (40) is configured to provide communications between the service center (40) and the patient intermediary device (30),
 b. the programming device (20) is configured to transmit the programming instructions to the service center (40), and
 c. the service center (40) is configured to transmit the received programming instructions to the patient intermediary device (30).

10. The system of claim 7 wherein the programming device (20) is configured to transmit the programming instructions to the patient intermediary device (30) via the service center (40), the service center (40) including:
 a. a service center first interface (41) configured to receive the programming instructions from the programming device (20), and
 b. a service center second interface (45) configured to transmit the programming instructions to the patient intermediary device (30).

11. The system of claim 7 wherein:
 a. the programming device (20), patient intermediary device (30), and programmable personal medical device (10, 10') are all separate and spaced apart; and
 b. the patient intermediary device (30) and the programmable personal medical device (10, 10') are configured to wirelessly communicate at a range of up to approximately 5 meters.

12. A system for the remote programming of a programmable personal medical device, in particular an implantable medical device such as a cardiac pacemaker, defibrillator, or the like, including:
 i. a programming device (20),
 ii. a service center (40)
 iii. a patient intermediary device (30),
 iv. a programmable personal medical device (10, 10'),
 wherein:
 a. the programming device (20) is configured to:
  (1) accept input of programming instructions for the programmable personal medical device (10, 10'), and
  (2) thereafter transmit the programming instructions;

b. the service center (40) is configured to:
   (1) receive the programming instructions from the programming device (20), and
   (2) thereafter transmit the programming instructions;
c. the patient intermediary device (30) is configured to receive the programming instructions from at least one of:
   (1) the service center (40), and
   (2) the programming device (20),
   and thereafter transmit the programming instructions to the personal medical device (10, 10'),
d. the personal medical device (10, 10') includes a programmable controller (13) configured to control functions of the personal medical device (10, 10') in accordance with:
   (1) the programming instructions received from the patient intermediary device (30), and
   (2) programming instructions received:
      (a) from the programming device (20), and
      (b) not from the patient intermediary device (30); and
   and wherein programming instructions received from the programming device (20), and not from the patient intermediary device (30), have greater control over the functions of the personal medical device (10, 10') than programming instructions received from the patient intermediary device (30).

13. The system of claim 12, wherein:
a. the service center (4) has:
   (1) a service center first interface (41) configured to connect the service center (40) in communication with the programming device (20), and
   (2) a data memory (43) configured to store data associated with at least one personal medical device, and
b. wherein:
   (1) the programming device (20) is configured to communicate with the service center (40),
   (3) the programming device (20) is configured to request data associated with the personal medical device (10, 10') from the service center (40).

14. The system of claim 13 wherein:
a. the service center (40) is configured to provide communications between the service center (40) and the patient intermediary device (30),
b. the programming device (20) is configured to transmit the programming instructions to the service center (40), and
c. the service center (40) is configured to transmit the received programming instructions to the patient intermediary device (30).

15. The system of claim 12 wherein the programming device first interface (21) is configured to transmit the programming instructions to the patient intermediary device (30) via the service center (40), the service center (40) including:
a. a service center first interface (41) configured to receive the programming instructions from the programming device (20), and
b. a service center second interface (45) configured to transmit the programming instructions to the patient intermediary device (30).

16. The system of claim 12 wherein:
a. the programming device (20), patient intermediary device (30), and programmable personal medical device (10, 10') are all separate and spaced apart; and
b. the patient intermediary device first interface (31) and the personal device first interface (11) are configured to wirelessly communicate at a range of up to approximately 5 meters.

17. A system for the remote programming of a programmable personal medical device, in particular an implantable medical device such as a cardiac pacemaker, defibrillator, or the like, including:
i. a programming device (20),
ii. a patient intermediary device (30),
iii. a programmable personal medical device (10, 10'),
the programming device (20), patient intermediary device (30), and programmable personal medical device (10, 10') being spaced from each other, wherein:
a. the programming device (20) includes:
   (1) a programming unit (23) configured to accept input of programming instructions for the programmable personal medical device (10, 10');
   (2) a programming device first interface (21) in communication with the patient intermediary device (30) and transmitting the programming instructions thereto;
b. the patient intermediary device (30) includes:
   (1) an intermediary device second interface (33) receiving the programming instructions from the programming device (20),
   (2) an intermediary device first interface (31) transmitting the programming instructions to the personal medical device (10, 10'),
c. the personal medical device (10, 10') includes:
   (1) a personal device first interface (11) receiving the programming instructions:
      (a) from the programming unit (23) without the programming instructions being received by the patient intermediary device (30); and
      (b) from the intermediary device first interface (31),
   (2) a programmable controller (13) controlling functions of the personal medical device (10, 10') in accordance with the programming instructions received by the personal device first interface (11),
wherein any programming instructions sent by the programming device (20) to the personal medical device (10, 10') via the programming unit (23) include control parameters which are more limited than the control parameters of any programming instructions sent by the programming device (20) to the personal medical device (10, 10') other than via the programming unit (23).

18. The system of claim 17:
a. further including a service center (40) having:
   (1) a service center first interface (41) configured to connect the service center (40) in communication with the programming device (20), and
   (2) a data memory (43) configured to store data associated with at least one personal medical device,
b. wherein:
   (1) the programming device (20) further includes a programming device second interface (29) allowing communication between the programming device (20) and the service center (40),
   (2) the programming unit (23) and the input unit (25) cooperate to request data associated with the personal medical device (10, 10') from the service center (40).

19. The system of claim 18 wherein:
a. the service center (40) has a service center second interface (45) configured to provide communications between the service center (40) and the patient intermediary device (30),
b. the programming device (20) is configured to transmit the programming instructions to the service center (40), and c. the service center (40) is configured to transmit the received programming instructions to the patient intermediary device (30).

20. The system of claim 17 wherein the programming device first interface (21) is configured to transmit the programming instructions to the patient intermediary device (30) via a service center (40), the service center (40) including:

a. a service center first interface (41) configured to receive the programming instructions from the programming device first interface (21), and b. a service center second interface (45) configured to transmit the programming instructions to the intermediary device second interface (33).

21. The system of claim 17 wherein the patient intermediary device first interface (31) and the personal device first interface (11) are configured to wirelessly communicate at a range of up to approximately 5 meters.

* * * * *